United States Patent [19]

Evtodienko et al.

[11] Patent Number: 6,043,096
[45] Date of Patent: Mar. 28, 2000

[54] DEVICE AND METHOD FOR THE DETERMINATION OF WATER

[75] Inventors: Yuriy Vladimirovich Evtodienko; Boris Ivanovich Medvedev, both of Moscow Region, Russian Federation

[73] Assignee: Environmental Test Systems, Inc., Elkhart, Ind.

[21] Appl. No.: 09/012,764

[22] Filed: Jan. 23, 1998

Related U.S. Application Data

[63] Continuation-in-part of application No. 08/732,021, Oct. 16, 1996, abandoned.

[51] Int. Cl.⁷ .................................................. G01N 33/18
[52] U.S. Cl. ..................................... 436/39; 436/1; 436/3; 436/41; 422/61; 73/61.43
[58] Field of Search ........................... 422/56, 61; 436/1, 436/3, 39, 40, 41, 42; 73/61.43

[56] References Cited

U.S. PATENT DOCUMENTS

| | | | |
|---|---|---|---|
| 2,761,312 | 9/1956 | Line et al. ................................. | 436/40 |
| 3,232,710 | 2/1966 | Rieckmann et al. ................. | 436/169 X |
| 3,389,967 | 6/1968 | Hrabinski ................................. | 436/40 |
| 3,680,364 | 8/1972 | Carrier ....................................... | 73/73 |
| 3,788,128 | 1/1974 | Strohecker ................................ | 73/73 |
| 3,901,657 | 8/1975 | Lightfoot ............................. | 436/170 X |
| 4,061,468 | 12/1977 | Lange et al. ........................ | 436/170 X |
| 4,184,445 | 1/1980 | Burrows ................................. | 116/206 |
| 4,806,353 | 2/1989 | Thomas ................................... | 424/141 |
| 4,990,284 | 2/1991 | Lauterbach et al. ................. | 252/408.1 |
| 5,224,373 | 7/1993 | Williams et al. ....................... | 73/29.02 |
| 5,290,516 | 3/1994 | Greco et al. .......................... | 436/41 X |

*Primary Examiner*—Lyle A. Alexander
*Attorney, Agent, or Firm*—Zarley, McKee, Thomte, Voorhees & Sease

[57] ABSTRACT

A test device and method is described for directly determining the liquid phase water content of organic solvents and indirectly the liquid phase water content of solids. The device and method utilize a reagent composition consisting basically the dried residue of a mixture of a colorimetric indicator material, preferably a cobaltous or cuprous salt, and a polymeric water barrier material, such mixture incorporated into a matrix which is contacted with or immersed into the liquid test sample, removed therefrom and the color change of the test composition correlated with a standard color chart to give a quantitative result of the amount of water in the test sample. When the method is applied to solids, the water must first be extracted from the solid using a substantially anhydrous extracting fluid such as reagent alcohol.

16 Claims, No Drawings

DEVICE AND METHOD FOR THE DETERMINATION OF WATER

RELATIONSHIP TO COPENDING APPLICATIONS

This application is a continuation-in-part of U.S. application Ser. No. 08/732,021 filed Oct. 16, 1996 now abandoned.

FIELD OF THE INVENTION

The present invention relates to a dry reagent test device and method for directly determining the water content of liquids and indirectly the water content of solids. The dry reagent test device is typically a flat matrix material containing the dried residue of a colorimetric test composition which responds quantitatively to the water content of fluids. The method comprises contacting the device with water dissolved in a water miscible solvent or in the case of determining water in solids, first extracting the water with an anhydrous water miscible solvent and thereafter contacting the extractant with the test device.

BACKGROUND OF THE INVENTION

The determination of water in various liquids and solids is almost universally included in a complete chemical analysis, the rationale for and importance of such determination being peculiar to the material being tested. In some instances water content can adversely affect the material while in others it can enhance the performance or value of the material. For example, in the automotive fluid area, the water content of the ethylene glycol cooling fluid can dramatically enhance the freezing point of the mixture while water in the ABS brake fluid can adversely affect the performance of the auto braking system.

Moreover, the water content of solid materials such as chemicals and food stuffs can positively or negatively affect the taste, performance and/or stability thereof. Accordingly, there is a need for an easy to use, safe, and reasonably accurate chemical method and test device for determining the water content of a large variety of materials. The present test meets such needs directly for determining the water content of water miscible solvents and indirectly for determining the water content of solids which can be extracted with water miscible solvents.

As noted above, the water content of fluids used in anti-locking brake systems (ABS) is of particular interest. Such fluids commonly use glycol derivatives, such as triethylene glycol monomethyl ether, as the liquid base. It has been found that over a period of time such fluids absorb moisture which in turn lowers the boiling point of the fluid. When this happens, especially during warm weather and when brakes are continuously used such as in a long downhill descent, the fluid could boil, resulting in a complete loss of the braking system. Consequently, it is becoming necessary to routinely test such fluids for water content and discard the material when it reaches a predetermined level of water contamination.

DESCRIPTION OF THE PRIOR ART

Generally, water analysis is either done by testing for water in the vapor phase (humidity) or for water in the liquid phase as a component of either another liquid or a solid material. Testing for humidity is probably the most common type of water determination and is usually accomplished using an instrument known as a hygrometer or a simple chemical test device using an inorganic metal salt impregnated into a paper matrix which responds to water vapor to give a colored response. The metal salt devices date back to the 1940's and have been the subject matter of numerous patent and literature references. Exemplary of the patent references are U.S. Pat. Nos. 2,460,065 to 2,460,074. More specifically, U.S. Pat. No. 4,034,609 which discloses and claims a more sophisticated device which gives a digital indicia of humidity using such salts also recites some of the many patent references as well as literature references in column 3, lines 48 to 64.

The second type of testing, commonly used in the analytical chemistry laboratory, is for the determination of the liquid water content of various solid or liquid materials using a chemical test reagent system and possibly an instrumental readout system for measuring the response of the reagent system. Exemplary of the sample materials that are commonly tested for water content are grains, organic chemicals, solvents, oils, biological materials and so forth. This type of chemical water testing can also be further broken down into the actual technique used to determine the water content of the material being tested. The present invention deals with a colorimetric chemical method for determining the liquid water content of a sample and the prior art recited herein will be limited to such chemical methods. Instruments will not be addressed in this discussion of the prior art.

Chemical methods for determining liquid phase water date back to the early part of the twentieth century; however, by far the most popular and accurate chemical method for the determination of water is based on the so-called Karl Fischer reagent. This method was first introduced in 1935 and is the subject matter of several books including the classic text by Mitchell and Smith titled "Aquametry", Interscience Publishers, Inc., New York, 1948. This textbook gives an excellent background and history of water determinations including the technical details of the Karl Fischer methodology as well as other chemical methodologies, including the use of inorganic metal salts for determining the vapor phase water content of hydrocarbon gases (Chapter 1, page 8).

In 1956, Line et al. disclosed and claimed in U.S. Pat. No. 2,761,312 a test device and method for determining low levels of water in such water immiscible organic liquids such as halogenated refrigerants, oils, gasoline and the like. The device consisted of anhydrous cobaltous bromide incorporated into a white cellulosic material. The Line et al. patent specification recited extensive prior art relating to the use of metal salts which change color in passing from the anhydrous to the hydrated state when being exposed to significant amounts of atmospheric moisture.

U.S. Pat. No. 3,389,967 to Hrabinski discloses and claims a process and device for determining trace amounts of water in organic solvents such as hexane, heptane and benzene. The device consists of a test paper impregnated with methyl orange coated with particulate phosphorus pentoxide. In the experimental part of Hrabinski's disclosure (Example 12), he indicates that the paper strip device could possibly be protected from atmospheric moisture degradation by applying a heptane solution of "butyl polymer" and drying. He goes on to state that such a procedure did not work.

More recently, U.S. Pat. No. 5,224,373 to Williams et al. discloses and claims a multilayer humidity in air sensor which comprises a first water vapor barrier material on one side of a layer sensitive to water vapor and a third layer of water vapor permeable plastic material. In use the sealed system is exposed to humid air which permeates the water vapor permeable layer to reach the humidity sensing layer to give a color response to the degree of exposure to water vapor.

Finally, U.S. Pat. No. 5,520,041 to Haswell discloses a medical sample system which utilizes the Williams et al. cobaltous chloride humidity sensing device and further refers to U.S. Pat. 2,214,354 to Snelling which discloses a composition which absorbs moisture which in turn activates a dyestuff to give an visual indication of the moisture present in the atmosphere.

SUMMARY OF THE INVENTION

The present invention relates to an easy to use, disposable, dip and read test device for determining the amount of water present in various water miscible liquid and solid materials. When used to determine the liquid phase water content of solids, the test sample must first be extracted with a water miscible anhydrous solvent such as absolute alcohol and then the solution of water in solvent contacted with the test device. The test device itself consists essentially of a liquid sample absorbent matrix containing the dried solids of a water sensitive reagent system which, in use, is contacted with the sample to be tested, removed therefrom and the developed color compared to a color chart, other indicia of water concentration or algorithm to give a quantitative value of the amount of water present in the sample. The reagent system comprises 1), a chemical indicator material which is responsive to water to give a color change proportional to the amount of water present in the sample and 2). A polymeric water barrier material which functions to allow the water in the sample to react with the indicator material and to protect the indicator material during processing and use.

DESCRIPTION OF THE PREFERRED EMBODIMENTS

Dip and read test devices, commonly known as reagent strips, have been in extensive use, especially in the medical area, for the past thirty to forty years. Some simpler test strips, such as litmus paper, go back even much further in time. Such devices commonly utilize an absorbent matrix consisting of either paper or other flat synthetic liquid absorbent fibrous materials or membranes into or onto which a colorimetric reagent system can be incorporated and subsequently dried. The resulting structure can be either attached to a plastic handle or used by itself to contact the fluid being tested, withdrawn and the resulting color change read and interpreted.

In its simplest form, the reagent system of the present invention comprises two essential components. The first is a water sensitive indicator material which responds to the presence thereof by either changing color in proportion to the amount of water present or by simply increasing in color intensity. The term "change in color" therefore is intended to encompass either an actual change from one color to another, such as in changing from blue to pink or simply changing from a light shade of blue to a more intense shade of the same blue color. Either way, the change in color must be proportional to the amount of water present in the sample being tested.

The indicator materials of the present invention are basically metal salts which give a color response to the presence of water. Preferred indicator materials are the cobaltous and the cuprous halides and thiocyanates such as cobaltous bromide ($Br_2Co$), cobaltous chloride ($Cl_2Co$), cobaltous iodide ($I_2Co$), cuprous bromide ($Br_2Cu$), cuprous chloride ($Cl_2Cu$), cuprous iodide ($I_2Cu$), and cobaltous thiocyanate [$Co(CNS)_2$]. Other metal salts which respond in a similar manner may also be used in the present invention. An amount of indicator to give a visual response to the concentration of water present is usually used, the preferred amount to respond to about five percent water in the liquid phase sample solution is from about 40 mg/ml to about 100 mg/ml of metal halide as used in the impregnating solution. Obviously, the amount of actual indicator in the matrix depends upon the size, absorbency and volume of the matrix. Combinations of metal salts to give the best color changes in response to water or to eliminate or obviate color interference in or by the sample solution may certainly be advantageously utilized.

The second essential component of the present reagent composition is a polymeric water barrier material. While the exact chemical and/or physical mechanism and function of this essential component is not known with certainty, it appears that it allows the water in the sample solution to react with the indicator material when the device is contacted with or immersed in the sample fluid but prevents interference from atmospheric water vapor once the test device has been removed from the sample solution and the color development allowed to go to completion. This is especially important when the device is used as a field test and is exposed to very high humidity levels. This second component also allows the more facile processing of the test device during manufacturing.

The water barrier materials of the present invention are polymeric substances which have limited solubility in water and are soluble in a substantially anhydrous solvent. The polyethylene and polypropylene glycols having molecular weights of from about 400 to about 35,000 have been found to be particularly useful as water barrier materials with the preferable molecular weight being from about 400 to about 2000. Other barrier materials which have been found to be useful in the present invention are poly (vinyl chloride) (PVC) and poly (vinyl pyrrolidone) (PVP). Combinations of various water barrier materials may also be advantageously used in formulating the composition of the present invention.

The matrix which incorporates the test composition of the present invention is basically a flat, relatively thin, sheet or roll of material which has absorbent or bibulous properties. Advantageously, this matrix can be made from natural or synthetic fibrous substances such as filter paper, polyester, glass fibers, membranes, and so forth. Usual methods may be used to incorporate or impregnate the test composition into the matrix; however, since this is a test device for determining water, precautions must be in place to ensure that all of the raw materials are dry and that the environment in which the processing takes place has a relative humidity of less than about 25% percent.

After incorporating the reagent system into the matrix, it is preferable to attach an appropriate sized area of the matrix to a strip of water and solvent impervious plastic material, which strip serves as a handle to facilitate immersing the matrix and reagent into the sample being tested. Such handle also serves to isolate the actual test reagent from being contaminated or ruined by contacting the reagent area with moisture from the fingers of the analyst.

The method of using the device to test for water in a liquid test sample is fairly straightforward. The test device is simply immersed into the fluid being tested, removed and after a predetermined length of time, usually less than a minute, the color of the test area is compared to a color chart which has been prepared using a standard set of water concentrations in an acceptable anhydrous solvent. An alternative method of use would be to use a reflectance device to measure the color developed on the strip and interpret such color in terms of water concentration in the sample being tested.

As previously noted, when solid materials such as food stuffs are being tested for water content, the sample must first be pulverized and the water extracted therefrom using an anhydrous water miscible solvent. After filtering, if necessary, the sample is tested in the usual manner. Obviously, precautions must be take to protect the sample and test area from environmental moisture contamination.

Actual processing conditions and testing parameters are exemplified by but should not be limited to the Examples which follow.

EXAMPLE 1

A first reagent composition was prepared by dissolving 500 mg of cobaltous iodide ($CoI_2$) and 0.2 ml polypropylene glycol (m.w.425) in 5 ml of reagent ethyl alcohol. A length of Whatman F322-02 paper was dipped into this mixture and dried at 110° C. for ten minutes. Upon dipping into the mixture the paper was teal blue in color and upon drying became light lime green after drying. The dried paper was cut into 0.2 by 0.2 in. squares and using double faced adhesive tape such squares attached to the end of a strip of reasonably rigid sheet of plastic material 3.25 in. by 0.2 in. All processing of such strips was done in a room having a relative humidity of less that 10%. The strips were stored in tightly capped bottles with desiccant.

A second composition was prepared as detailed next above except that the polypropylene glycol was omitted. Reagent strips were made as described above and also stored in bottles with desiccant. In preparing this second batch of strips, it was noted that within seconds the paper started to turn pink and upon drying the strips became a dark gray color. Upon removal from the drying oven, the strips became a light lime green color but developed pink and red splotches.

The strips containing the polymer were then dipped into brake fluid samples (DOT 3 and 4) known to have a water content of 0, 1, 2, 3, 4, and 5%. Such strips changed from gray green to light olive green depending on the amount of water in the brake fluid. The strips which did not have the polymer changed to a yellowish green and could not be used against a series of standard color blocks. When both sets of reacted strips were exposed to atmosphere moisture of approximately 25% relative humidity, the strips containing the polymer were unchanged for six hours while the strips which did not contain the polymer changed color significantly within three hours.

EXAMPLE 2

The above example was repeated except that polyethylene glycol (m.w. 35,000) was substituted for the polypropylene glycol. When processing and when dipped into varying concentrations of water in brake fluid, the strips reacted in a similar way to those in Example 1.

EXAMPLE 3

Varying concentrations of $Al(NO_3)_3 \times 9H_2O$ were dissolved in reagent ethyl alcohol to give 1%, 3% and 5% water content. The samples were tested with the strips containing the vapor phase barrier of Example 1. The color change from gray green to light green indicated the water content of the solution contributed by the hydrated aluminum nitrate.

What is claimed is:

1. A test device for determining liquid-phase water content of an organic solvent comprising
    a) an absorbent matrix incorporating
    b) a dried residue of a reagent composition wherein the reagent composition comprises:
        i) a colorimetric indicator material quantitatively responsive to the presence of water selected from the group consisting of cobaltous and cuprous halides and thiocyanates and combinations thereof; and,
        ii) a polymeric water vapor barrier material effective to allow in the liquid-phase water of the solvent while substantially preventing interference from vapor-phase water of air wherein the polymeric material is selected from the group consisting of polyethylene glycol, polypropylene glycol, polyvinyl chloride and polyvinyl pyrrolidone.

2. A test device as in claim 1 wherein the polymeric material is selected from the group consisting of polyethylene glycol and polypropylene glycol.

3. A test device as in claim 2 wherein the polymeric material has a molecular weight of from about 400 to about 35,000.

4. A test device as in claim 3 wherein the polymeric material has a molecular weight of from about 400 to about 2000.

5. A test device as in claim 1 wherein the indicator material is selected from the group consisting of cobaltous chloride and cobaltous iodide.

6. A test device as in claim 5 wherein the indicator material is cobaltous iodide.

7. A test device as in claim 1 wherein the organic solvent is selected from the group consisting of ethylene and propylene glycols.

8. A colorimetric method for quantitatively determining the liquid phase water content of an organic solvent sample, the method comprising:
    a) contacting the solvent sample for a predetermined time with a dip-and-read test device comprising
        i) a fluid absorbent matrix incorporating
        ii) a dried residue of a test composition wherein the test composition comprises
            1) a colorimetric indicator material selected from the group consisting of cobaltous halides, cuprous halides, cobaltous thiocyanates, cuprous thiocyanates, and combinations thereof, and
            2) a polymeric water vapor barrier material effective to allow in the liquid-phase water of the solvent while substantially preventing interference from vapor-phase water of air wherein the polymeric material is selected from the group consisting of polyethylene glycol, polypropylene glycol, polyvinyl chloride, and polyvinyl pyrrolidone;
    b) removing the test device from contact with the solvent sample and allowing the color response of the indicator material to develop in the open atmosphere;
    c) measuring the degree of color response of the indicator material; and,
    d) using a correlating means, determining the amount of liquid water in the solvent sample from the degree of color response of the indicator material.

9. A method as in claim 8 wherein the polymeric water barrier material is selected from the group consisting of polyethylene glycol and polypropylene glycol.

10. A method as in claim 9 wherein the polymeric water barrier material has a molecular weight of about from 400 to 35,000.

11. A method as in claim 9 wherein the polymeric water barrier has a molecular weight of about 400 to 2000.

12. A method as in claim 8 wherein the colorimetric indicator is selected from the group consisting of cobaltous iodide, cobaltous chloride and combinations thereof.

13. A method as in claim 12 wherein the colorimetric indicator is cobaltous iodide.

14. A method as in claim 8 wherein the organic solvent is selected from the group consisting of ethylene and propylene glycols.

15. A method as in claim 8 wherein the organic solvent sample results from extracting a solid, water-containing material with an organic solvent.

16. A method as in claim 15 wherein the organic solvent is an anhydrous alcohol.

* * * * *